United States Patent
Johns et al.

(10) Patent No.: US 10,239,840 B2
(45) Date of Patent: Mar. 26, 2019

(54) BENZOAZEPINE DERIVATIVES

(71) Applicant: ViiV HEALTHCARE UK LIMITED, Brentford, Middlesex (GB)

(72) Inventors: Brian Alvin Johns, Research Triangle Park, NC (US); Lita S. Suwandi, Research Triangle Park, NC (US); Emile Johann Velthuisen, Research Triangle Park, NC (US); Jason Gordon Weatherhead, Research Triangle Park, NC (US)

(73) Assignee: VIIV HEALTHCARE UK LIMITED, Brentford, Middlesex (GB)

( * ) Notice: Subject to any disclaimer, the term of this patent is extended or adjusted under 35 U.S.C. 154(b) by 0 days.

(21) Appl. No.: 15/759,363

(22) PCT Filed: Sep. 14, 2016

(86) PCT No.: PCT/IB2016/055462
§ 371 (c)(1),
(2) Date: Mar. 12, 2018

(87) PCT Pub. No.: WO2017/046707
PCT Pub. Date: Mar. 23, 2017

(65) Prior Publication Data
US 2018/0179162 A1    Jun. 28, 2018

Related U.S. Application Data

(60) Provisional application No. 62/219,687, filed on Sep. 17, 2015.

(51) Int. Cl.
| | |
|---|---|
| C07D 223/16 | (2006.01) |
| C07D 405/14 | (2006.01) |
| C07D 405/10 | (2006.01) |
| A61P 31/18 | (2006.01) |
| A61K 31/55 | (2006.01) |

(52) U.S. Cl.
CPC ............ C07D 223/16 (2013.01); A61K 31/55 (2013.01); A61P 31/18 (2018.01); C07D 405/10 (2013.01); C07D 405/14 (2013.01)

(58) Field of Classification Search
CPC .. C07D 223/16; C07D 405/14; C07D 405/10; A61K 31/55; A61P 31/18
See application file for complete search history.

(56) References Cited

U.S. PATENT DOCUMENTS

2015/0361093 A1* 12/2015 Tomita ................. C07D 495/14
514/211.04

FOREIGN PATENT DOCUMENTS

| WO | WO 2013/134142 A1 | 9/2013 |
|---|---|---|
| WO | WO 2015/127003 A1 | 8/2015 |
| WO | WO 2016/005878 A1 | 1/2016 |

* cited by examiner

*Primary Examiner* — John M Mauro
(74) *Attorney, Agent, or Firm* — Robert H. Brink; Kathryn A. Lutomski; Edward R. Gimmi

(57) ABSTRACT

Compounds of Formula I are disclosed and methods of treating viral infections with compositions comprising such compounds.

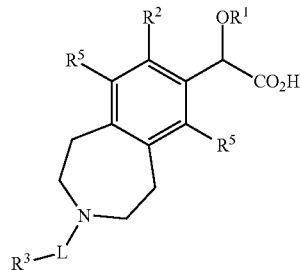

Formula I

11 Claims, No Drawings

BENZOAZEPINE DERIVATIVES

This application is a § 371 of International Application No. PCT/IB2016/055462, filed 14 Sep. 2016, which claims the benefit of U.S. Provisional Application No. 62/219,687, filed 17 Sep. 2015.

CROSS-REFERENCE TO RELATED APPLICATIONS

This application claims priority to Provisional Patent Application U.S. Ser. No. 61/219,687 filed Sep. 17, 2015, hereby incorporated by reference in its entirety.

FIELD OF THE INVENTION

The present invention relates to substituted benzoazepine compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required because of undesirable drug-drug interactions; drug-food interactions; non-adherence to therapy; and drug resistance due to mutation of the enzyme target.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur. The emergence of multidrug-resistant HIV-1 isolates has serious clinical consequences and must be suppressed with a new drug regimen, known as salvage therapy.

Current guidelines recommend that salvage therapy includes at least two, and preferably three, fully active drugs. Typically, first-line therapies combine three to four drugs targeting the viral enzymes reverse transcriptase and protease. One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase inhibitors. However, resistance to all three new drug classes has already been reported both in the lab and in patients. Sustained successful treatment of HIV-1-infected patients with antiretroviral drugs will therefore require the continued development of new and improved drugs with new targets and mechanisms of action.

For example, over the last decade HIV inhibitors have been reported to target the protein-protein interaction between HIV-1 integrase and Lens Epithelium Derived Growth Factor/p75 ("LEDGF"). LEDGF is a cellular transcriptional cofactor of HIV-1 integrase that promotes viral integration of reverse transcribed viral cDNA into the host cell's genome by tethering the preintegration complex to the chromatin. Because of its crucial role in the early steps of HIV replication, the interaction between LEDGF and integrase represents another attractive target for HIV drug therapy.

SUMMARY OF THE INVENTION

Briefly, in one aspect, the present invention discloses compounds of Formula I:

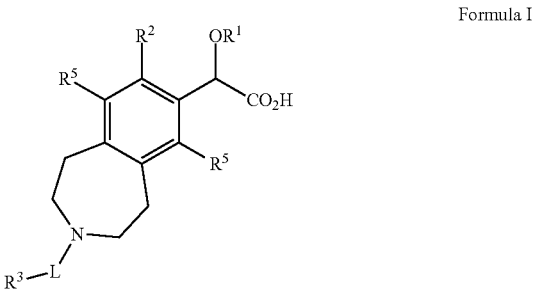

Formula I wherein:

$R^1$ is $C_{1-6}$alkyl;

$R^2$ is $C_{5-14}$aryl, $C_{3-7}$cycloalkyl, $C_{3-7}$cycloalkenyl, $C_{3-9}$heterocycle, or $C_{5-9}$heteroaryl, wherein each $R^2$ group is optionally substituted by one to four substituents selected from halo, $C_{1-6}$alkyl, $C_{1-6}$heteroalkyl, or $C_{1-6}$alkylene or $C_{1-6}$heteroalklylene wherein said $C_{1-6}$alkylene or $C_{1-6}$hetereoalklylene are bonded to adjacent carbon atoms on said $C_{5-14}$aryl, $C_{3-7}$cycloalkyl, $C_{3-7}$cycloalkenyl, $C_{3-9}$heterocycle, or $C_{5-9}$heteroaryl to form a fused ring;

L is a bond, —$CH_2(CO)$—, —$C_{1-3}$alkylene-, —$SO_2$—, —C(O)—, —C(S)—, —C(NH)—, —C(O)NH—, —C(O)NHCH_2$—, —C(O)N—, —$C(O)OCH_2$—, —C(O)O—, —C(O)C(O)—, —$SO_2$—NH—, or —$CH_2C(O)$—;

$R^3$ is H, CN, $C_{1-6}$alkyl, $C_{5-14}$aryl, $CH_2C_{5-14}$aryl, $CH_2C_{3-7}$cycloalkyl, $C_{3-7}$cycloalkyl, $C_{3-7}$spirocycloalkyl, $C_{3-7}$cycloalkenyl, $C_{3-9}$heterocycle, or $C_{5-9}$heteroaryl, wherein each $R^3$ group is optionally substituted by one to four substituents selected from halo, $C_{1-6}$alkyl, $C_{2-8}$bridgedheterocycle, $C_{3-7}$cycloalkyl, $C_{1-3}$fluoroalkyl, —$OC_{1-6}$alkyl, —$C(O)R^4$, —$C(O)NR^4$, —$C(O)NHR^4$, $C_{5-14}$aryl, $C_{1-6}$heteroalkyl, —$B(OH)_2$, $C_{3-9}$heterocycle, $C_{5-6}$heteroaryl, —$C(O)OC_{1-6}$alkyl, or two substituents bonded to adjacent atoms may bond together to form a fused ring and that fused ring may optionally be substituted with $R^4$, wherein $R^4$ is CN, halo, —$OC_{1-6}$alkyl, $C_{1-6}$alkyl, $C_{3-7}$cycloalkyl, $C_{3-9}$heterocycle, or $C_{5-14}$aryl;

each $R^5$ is independently H, halogen, $C_{1-6}$alkyl, or $C_{3-7}$cycloalkyl, wherein each $C_{1-6}$alkyl and $C_{3-7}$cycloalkyl may optionally be substituted with 1-3 halogen atoms; and and wherein each heterocycle, heteroaryl, heteroalkyl, and heteroalkylene comprises one to three heteroatoms selected from S, N, B, or O.

In another aspect the present invention discloses pharmaceutically acceptable salts of the compounds of Formula I.

In another aspect, the present invention discloses pharmaceutical compositions comprising a compound of Formula I or a pharmaceutically acceptable salt thereof.

In another aspect, the present invention discloses a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

DETAILED DESCRIPTION OF THE INVENTION

Preferably $R^1$ is $C_{1-6}$alkyl. Most preferably, $R^1$ is t-butyl.

Preferably $R^2$ is optionally substituted phenyl. Most preferably, $R^2$ is phenyl substituted by one to four substituents selected from fluorine, methyl, —$CH_2CH_2CH_2O$— wherein said —$CH_2CH_2CH_2O$— is bonded to adjacent carbon atoms on said phenyl to form a bicyclic ring, or —$NHCH_2CH_2O$— wherein said —$NHCH_2CH_2O$— is bonded to adjacent carbon atoms on said phenyl to form a bicyclic ring.

Preferably L is —C(O)—.

Preferably $R^3$ is $C_{1-6}$alkyl, phenyl, naphthyl, cyclopentyl, cyclohexyl, pyridyl, or tetrahydropyranyl, each of which is optionally substituted by 1-3 substituents selected from halogen, $C_{1-6}$alkyl, —$OC_{1-6}$alkyl, $C_{1-3}$fluoroalkyl, or phenyl.

Preferably each $R^5$ is methyl.

Preferably the stereochemistry on the carbon to which $OR^1$ is bound is as depicted below.

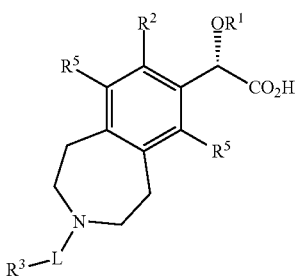

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

In one embodiment of the method of this invention, the viral infection is a viral infection in a human. In one embodiment, the viral infection is a viral infection mediated by the HIV virus.

EXAMPLES

The compounds of this invention may be made by a variety of methods, including well-known standard synthetic methods. Illustrative general synthetic methods are set out below and then specific compounds of the invention are prepared in the working examples.

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=aqueous
μL=microliters
μM=micromolar
NMR=nuclear magnetic resonance
boc=tert-butoxycarbonyl
br=broad
Cbz=benzyloxycarbonyl
d=doublet
δ=chemical shift
° C.=degrees celcius
DCM=dichloromethane
dd=doublet of doublets
DMEM=Dulbeco's Modified Eagle's Medium
DMF=N,N-dimethylformamide
DMSO=dimethylsulfoxide
EtOAc=ethyl acetate
g=gram
h or hr=hours
HCV=hepatitus C virus
HPLC=high performance liquid chromatography
Hz=hertz
IU=International Units
$IC_{50}$=inhibitory concentration at 50% inhibition j=coupling constant (given in Hz unless otherwise indicated)

m=multiplet

M=molar

M+H[+]=parent mass spectrum peak plus H+ mg=milligram min=minutes mL=milliliter mM=millimolar mmol=millimole

MS=mass spectrum nm=nanomolar ppm=parts per million q.s.=sufficient amount s=singlet RT=room temperature sat.=saturated t=triplet TFA=trifluoroacetic acid Z=benzyloxycarbonyl

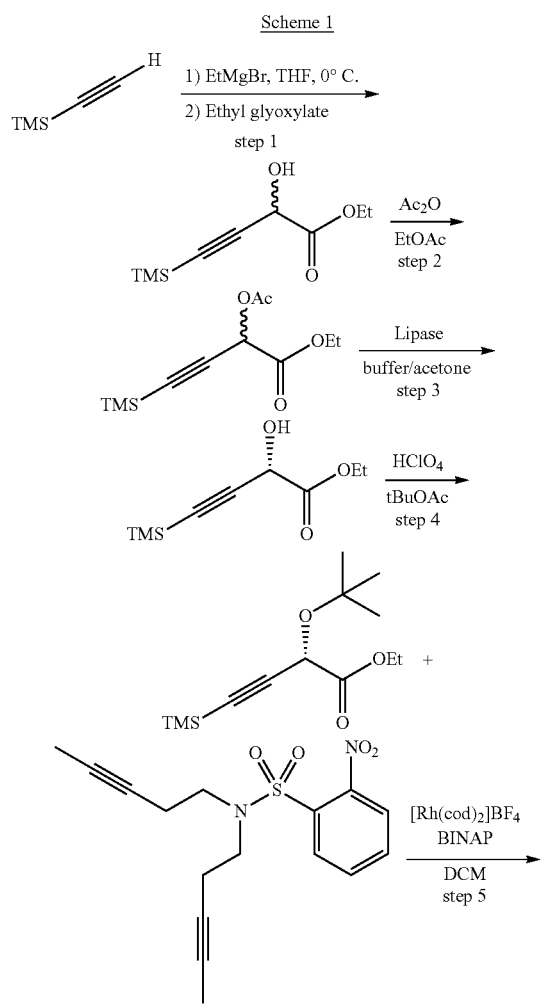

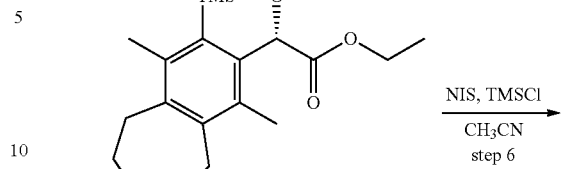

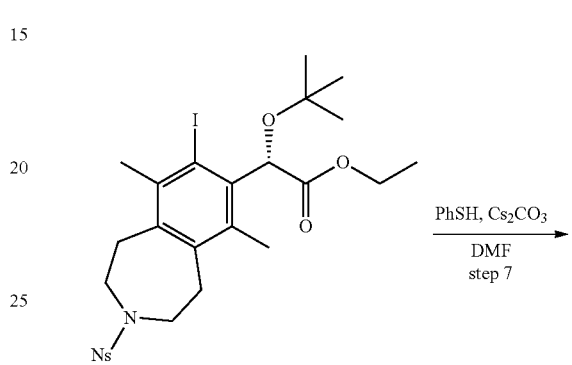

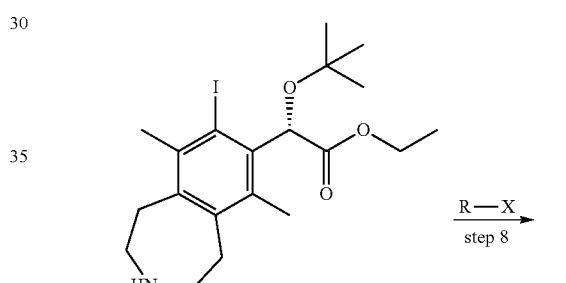

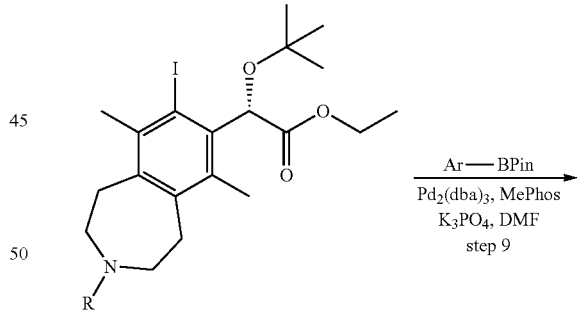

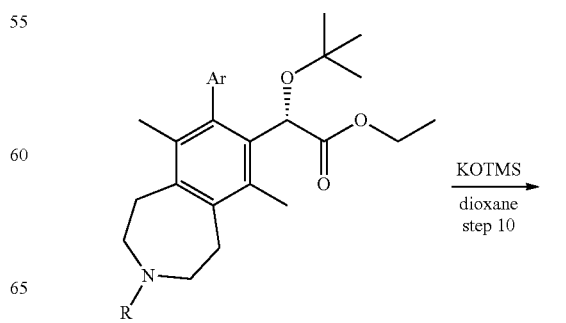

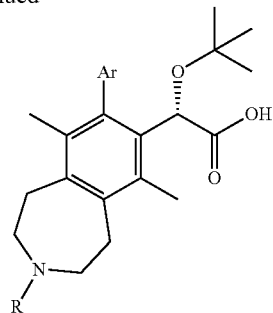

tography (0-50% DCM:hexanes). The residue was suspended in 1:1 ethyl ether/hexanes and cooled to 0° C. and the solids collected by vacuum filtration to afford the title compound (18 g, 51 mmol, 69% yield) as a white powder. $^1$H NMR (400 MHz, CHLOROFORM-d) δ ppm 8.0-8.2 (m, 1H), 7.6-7.8 (m, 3H), 3.5 (t, J=7.33 Hz, 4H), 2.4 (ddd, J=9.66, 4.99, 2.56 Hz, 4H), 1.7 (t, J=2.56 Hz, 6H). LCMS (ES+) (m/z): 335.3 (M+H).

Step 1

Ethyl 2-hydroxy-4-(trimethylsilyl)but-3-ynoate

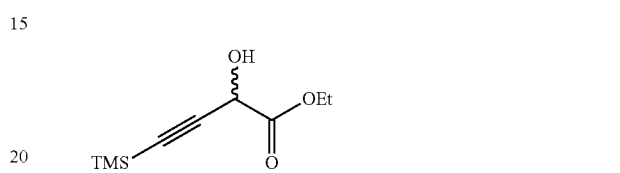

Example 1: (S)-2-(tert-butoxy)-2-((M)-8-(8-chloro-5-methylchroman-6-yl)-3-(3-fluorobenzoyl)-6,9-dimethyl-2,3,4,5-tetrahydro-1H-benzo[d]azepin-7-yl)acetic Acid To a solution of TMS-acetylene (250 g, 2.55 mol) in anhydrous THF (2.5 L) at 0° C. was added 3M EtMgBr/ether (933 mL, 2.80 mol) dropwise under an N$_2$ atmosphere while maintaining the inner temperature below 5° C. After stirring at 0° C. for 30 minutes, the suspension was added to an ice cold solution of 50% ethyl glyoxylate/toluene (624 g, 3.05 mol) in anhydrous THF (5 L) via cannula. After stirring at 0° C. for 1 hour, the mixture was quenched with saturated aqueous NH$_4$Cl solution (3 L) and extracted with EtOAc (2×1 L). The combined EtOAc solutions were concentrated at reduced pressure. The residue was diluted with EtOAc (3 L). The solution was washed with water (2×1 L) and brine (2×1 L), dried over Na$_2$SO$_4$ and concentrated in vacuo. The crude material was purified by flash chromatography (silica gel, 0-10% EtOAc/petroleum ether) to give the title compound (285 g, 56%) as a yellow oil. $^1$H NMR (400 MHz, CHLOROFORM-d) δ=4.83 (d, J=7.3 Hz, 1H), 4.34 (qq, J=7.2, 10.8 Hz, 2H), 3.02 (d, J=7.3 Hz, 1H), 1.34 (t, J=7.2 Hz, 3H), 0.22-0.16 (m, 9H).

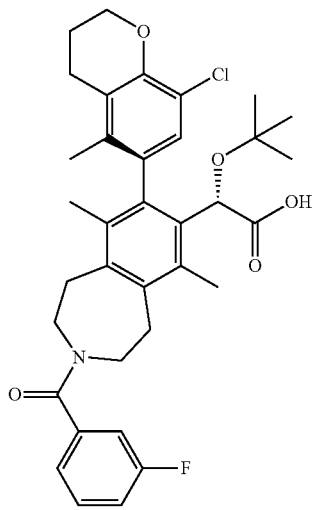

Step 2

Ethyl 2-acetoxy-4-(trimethylsilyl)but-3-ynoate

2-Nitro-N,N-di(pent-3-yn-1-yl)benzenesulfonamide

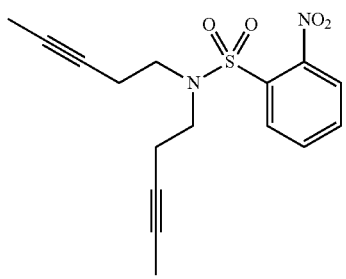 [SMILES: CC#CCCN(CCC#CC)S(=O)(=O)c1ccccc1[N+](=O)[O-]]

To a 10 L flask was added EtOAc (7.5 L) followed by Ac$_2$O (400 mL). After stirring at RT for 30 minutes the mixture was cooled to 0° C. and treated with another portion of Ac$_2$O (2.1 L). After 1 hour at 0° C., the solution was allowed to warm to RT. To the solution was added ethyl 2-hydroxy-4-(trimethylsilyl)but-3-ynoate (520 g, 2.60 mol). After stirring at RT for 1 hour the solution was washed with 1N aqueous NaOH (3×, 20 L total). The solution was then washed with brine (5 L), dried over Na$_2$SO$_4$ and concentrated to dryness at reduced pressure. The crude product was purified by flash chromatography (silica gel, 0-5% EtOAc/petroleum ether) to give the title compound (590 g, 94%) as a yellow oil. $^1$H NMR (400 MHz, CHLOROFORM-d)

A mixture of pent-3-yn-1-ol (60 g, 710 mmol), 2-nitrobenzenesulfonamide (15 g, 74 mmol), and triphenylphosphine (97 g, 370 mmol) in tetrahydrofuran (THF) (300 mL) was treated dropwise with DIAD (57.7 mL, 297 mmol). After 18 h, the reaction mixture was concentrated in vacuo. The resulting oil was treated with a 1:4 mixture of EtOAc: hexanes and the solids collected by filtration. The filtrate was concentrated in vacuo and purified by silica chroma- δ=5.69 (s, 1H), 4.36-4.21 (m, 2H), 2.19 (s, 3H), 1.32 (t, J=7.2 Hz, 3H), 0.25-0.15 (m, 9H).

Step 3

(S)-Ethyl 2-hydroxy-4-(trimethylsilyl)but-3-ynoate

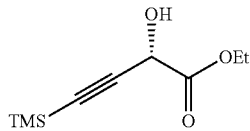

To a solution of ethyl 2-acetoxy-4-(trimethylsilyl)but-3-ynoate (150 g, 0.620 mol) in acetone (1.88 L) and phosphate buffer solution (pH 7.2, 7.5 L) was added Amano Lipase PS (75 g). After stirring at 20° C. overnight, the reaction mixture was diluted with water (2.5 L) and extracted with EtOAc (3 L). The layers were separated and the organic layer was washed with brine (3×, 10 L total volume), dried over $Na_2SO_4$, filtered and concentrated under reduced pressure to give the crude product. This material was purified by flash chromatography (silica gel, 0-10% EtOAc/petroleum ether) to afford the title compound (55 g, 44%) as a yellow oil. $^1$H NMR (400 MHz, CHLOROFORM-d) δ=4.83 (d, J=7.3 Hz, 1H), 4.34 (qq, J=7.2, 10.8 Hz, 2H), 3.02 (d, J=7.3 Hz, 1H), 1.34 (t, J=7.2 Hz, 3H), 0.22-0.16 (m, 9H).

Step 4

(S)-Ethyl 2-(tert-butoxy)-4-(trimethylsilyl)but-3-ynoate

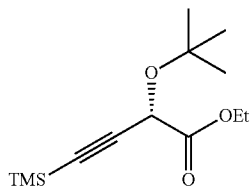

To a solution of (S)-ethyl 2-hydroxy-4-(trimethylsilyl)but-3-ynoate (100 g, 0.500 mol) in t-BuOAc (2.5 L) was added $HClO_4$ (41 mL, 0.500 mol) dropwise at RT. After stirring for 40 minutes, the mixture was quenched with $NaHCO_3$ powder, diluted with water (2 L) and extracted with EtOAc (2 L). The EtOAc solution was washed with brine, dried over $Na_2SO_4$, filtered and concentrated under reduced pressure to give the crude product. This material was purified by flash chromatography (silica gel, 0-5% EtOAc/petroleum ether) to afford the title compound (103 g, 81%) as a yellow oil. $^1$H NMR (400 MHz, CHLOROFORM-d) δ=4.72 (s, 1H), 4.33-4.20 (m, 2H), 1.31 (t, J=7.2 Hz, 3H), 1.28 (s, 9H), 0.17 (s, 9H).

Step 5

(S)-ethyl 2-(tert-butoxy)-2-(6,9-dimethyl-3-(2-nitrophenyl)sulfonyl)-8-(trimethylsilyl)-2,3,4,5-tetrahydro-1H-benzo[d]azepin-7-yl)acetate

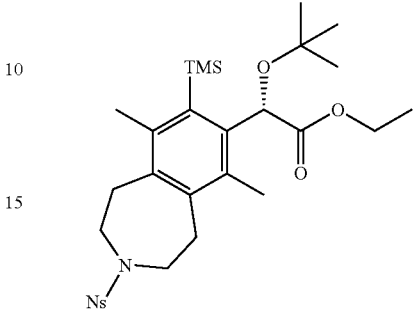

A suspension of BINAP (3.39 g, 5.44 mmol) and [Rh(cod)$_2$]BF$_4$ (2.21 g, 5.44 mmol) in dichloromethane (DCM) (100 mL) was bubbled with H$_2$ for 5 min and then maintained under an atmosphere of H$_2$. After 1 h, the H$_2$ balloon was removed and reaction mixture was bubbled with N$_2$ for 15 min. A solution of (S)-ethyl 2-(tert-butoxy)-4-(trimethylsilyl)but-3-ynoate (4.65 g, 18.1 mmol) in dichloromethane (10 mL) was added and the reaction flask lowered into a preheated oil bath at 45° C. A solution of 2-nitro-N,N-di(pent-3-yn-1-yl)benzenesulfonamide (15.2 g, 45.3 mmol) in dichloromethane (DCM) (100 mL) was then added dropwise over 120 min. After 1 h, the reaction mixture was cooled to ambient temperature and concentrated in vacuo. The residue was purified by silica chromatography (0-50% EtOAc-hexanes) to afford the title compound (5.3 g, 8.8 mmol, 49% yield) as a white foam. $^1$H NMR (400 MHz, CHLOROFORM-d) δ ppm 7.9-8.0 (m, 1H), 7.6-7.7 (m, 2H), 7.6-7.6 (m, 1H), 5.5 (br. s., 1H), 4.1-4.3 (m, 2H), 3.4-3.6 (m, 4H), 3.1 (t, J=5.04 Hz, 4H), 2.4 (s, 3H), 2.2 (s, 3H), 1.2-1.3 (m, 3H), 1.1 (s, 9H), 0.5 (s, 9H). LCMS (ES+) (m/z): 591.48 (M+H), 613.46 (M+Na).

Step 6

(S)-ethyl 2-(tert-butoxy)-2-(8-iodo-6,9-dimethyl-3-((2-nitrophenyl)sulfonyl)-2,3,4,5-tetrahydro-1H-benzo[d]azepin-7-yl)acetate

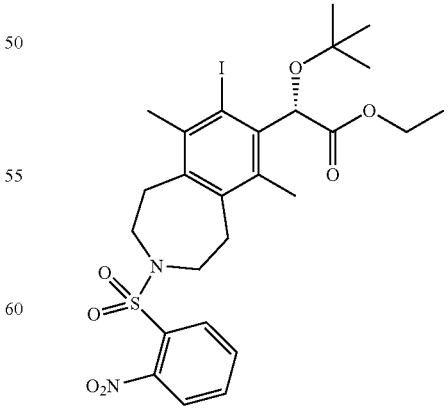

A solution of (S)-ethyl 2-(tert-butoxy)-2-(6,9-dimethyl-3-((2-nitrophenyl)sulfonyl)-8-(trimethylsilyl)-2,3,4,5-tetrahydro-1H-benzo[d]azepin-7-yl)acetate (6.1 g, 10 mmol) in acetonitrile (100 mL) was treated with N-iodosuccinimide (2.56 g, 11.4 mmol) and TMS-Cl (0.132 mL, 1.03 mmol). After 2 h, the reaction mixture was poured into an aqueous solution of $NaHCO_3$ and $Na_2S_2O_3$. The mixture was extracted with ethyl acetate (3×) and the combined organic layers were washed with saturated $Na_2S_2O_3$, washed with brine, dried over sodium sulfate, and concentrated in vacuo to afford the title compound (6.85 g, 10.3 mmol, 99% yield). $^1$H NMR (400 MHz, CHLOROFORM-d) δ ppm 7.8-8.0 (m, 1H), 7.7 (ddd, J=7.33, 5.40, 1.74 Hz, 2H), 7.6-7.6 (m, 1H), 5.9 (s, 1H), 4.2 (dd, J=11.72, 6.96 Hz, 2H), 3.5 (br. s., 2H), 3.4-3.5 (m, 2H), 2.9-3.3 (m, 4H), 2.5 (s, 3H), 2.3 (s, 3H), 1.2-1.2 (m, 12H). LCMS (ES+) (m/z): 667.34 (M+Na).

Step 7

(S)-ethyl 2-(tert-butoxy)-2-(8-iodo-6,9-dimethyl-2,3,4,5-tetrahydro-1H-benzo[d]azepin-7-yl)acetate

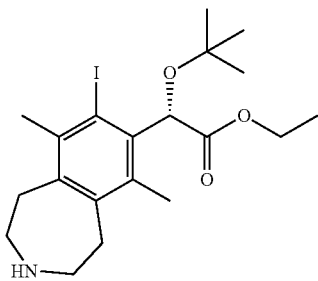 [SMILES: CCOC(=O)[C@@H](OC(C)(C)C)c1c(C)c2c(c(C)c1I)CCNCC2]

A solution of (S)-ethyl 2-(tert-butoxy)-2-(8-iodo-6,9-dimethyl-3-((2-nitrophenyl)sulfonyl)-2,3,4,5-tetrahydro-1H-benzo[d]azepin-7-yl)acetate (3.2 g, 5.0 mmol) and cesium carbonate (6.47 g, 19.9 mmol) in N,N-dimethylformamide (25 mL) was treated with thiophenol (2.05 mL, 19.9 mmol). After 2 h, the reaction mixture was diluted with 2-methyltetrahydrofuran, washed with 1M NaOH, washed with brine, dried over sodium sulfate, and concentrated in vacuo. The organic layer was concentrated in vacuo and the residue purified by silica chromatography (0-20% MeOH-DCM) to afford the title compound (1.65 g, 3.52 mmol, 70.9% yield) as an oil. $^1$H NMR (400 MHz, CHLOROFORM-d) δ ppm 5.9 (s, 1H), 4.2 (dd, J=10.53, 7.05 Hz, 2H), 3.0-3.2 (m, 2H), 2.8-3.0 (m, 6H), 2.6 (s, 3H), 2.3 (s, 3H), 1.9 (s, 1H), 1.2-1.4 (m, 12H). LCMS (ES+) (m/z): 460.29 (M+H).

Step 8

(S)-ethyl 2-(tert-butoxy)-2-(3-(3-fluorobenzoyl)-8-iodo-6,9-dimethyl-2,3,4,5-tetrahydro-1H-benzo[d]azepin-7-yl)acetate

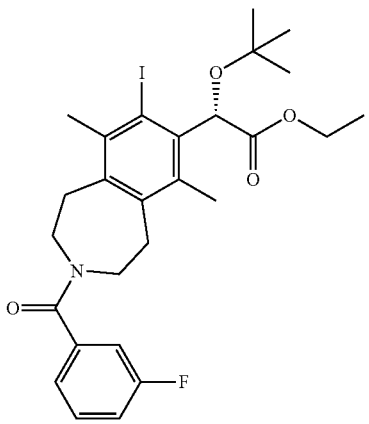 [SMILES: CCOC(=O)[C@@H](OC(C)(C)C)c1c(C)c2c(c(C)c1I)CCN(C(=O)c1cccc(F)c1)CC2]

An ice cold mixture of (S)-ethyl 2-(tert-butoxy)-2-(8-iodo-6,9-dimethyl-2,3,4,5-tetrahydro-1H-benzo[d]azepin-7-yl)acetate (1.63 g, 3.55 mmol), 3-fluorobenzoic acid (0.589 g, 4.08 mmol), and Hunig's base (2.48 mL, 14.2 mmol) in N,N-dimethylformamide (30 mL) was added 1-propanephosphonic acid cyclic anhydride (2.43 mL, 4.08 mmol, 50 wt. % solution in ethyl acetate) dropwise at such a rate that the temperature did not rise above 3° C. The mixture was stirred for 30 min and then warmed to ambient temperature. After 2 hours, the reaction mixture was quenched with brine and extracted 2-methyltetrahydrofuran (2×). The combined organic layers were washed with brine, dried over sodium sulfate, and concentrated in vacuo. The residue was purified by silica chromatography (0-20% ethyl acetate/dichloromethane) to afford (S)-ethyl 2-(tert-butoxy)-2-(3-(3-fluorobenzoyl)-8-iodo-6,9-dimethyl-2,3,4,5-tetrahydro-1H-benzo[d]azepin-7-yl)acetate (1.8 g, 3.1 mmol, 86% yield) as a white foam. $^1$H NMR (400 MHz, 80° C., DMSO-d$_6$) δ ppm 7.4 (d, J=6.04 Hz, 1H), 7.2 (br. s., 1H), 6.7 (d, J=7.33 Hz, 1H), 6.5-6.7 (m, 1H), 5.9 (s, 1H), 4.0-4.3 (m, 2H), 3.3-3.9 (m, 4H), 3.1 (br. s., 4H), 2.5 (br. s., 3H), 2.3 (br. s., 3H), 1.2-1.3 (m, 9H), 1.1 (t, J=7.05 Hz, 3H). LCMS (ES+) (m/z): 582.41 (M+H), 604.35 (M+Na).

Step 9

(S)-Ethyl 2-(tert-butoxy)-2-((M)-8-(8-chloro-5-methylchroman-6-yl)-3-(3-fluorobenzoyl)-6,9-dimethyl-2,3,4,5-tetrahydro-1H-benzo[d]azepin-7-yl)acetate

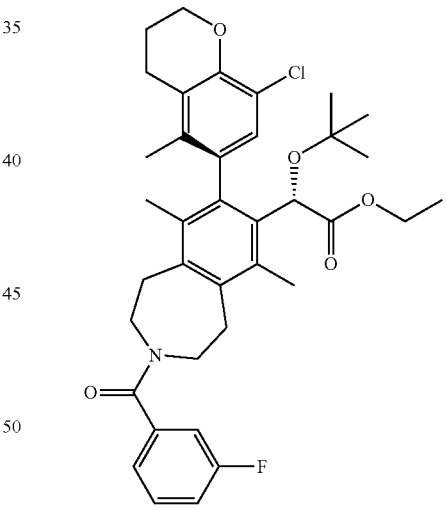

A solution of (S)-ethyl 2-(tert-butoxy)-2-(3-(3-fluorobenzoyl)-8-iodo-6,9-dimethyl-2,3,4,5-tetrahydro-1H-benzo[d]azepin-7-yl)acetate (108 mg, 0.186 mmol), 2-(8-chloro-5-methylchroman-6-yl)-4,4,5,5-tetramethyl-1,3,2-dioxaborolane (92 mg, 0.30 mmol), potassium phosphate tribasic (118 mg, 0.557 mmol), and MePhos (20 mg, 0.056 mmol) in N,N-dimethylformamide (DMF) (2 mL) was degassed with nitrogen for 5 min. Pd$_2$(dba)$_3$ (51 mg, 0.056 mmol) was added and the reaction vial placed into a heating block that was preheated to 90° C. After 2 h, the reaction mixture was cooled to ambient temperature and poured into a 1:1 mixture of water and ethyl acetate. The mixture was filtered through a cotton plug and the layers separated. The aqueous layer was extracted EtOAc (2×) and the combined organic layers were washed with brine, dried over sodium sulfate, and concentrated in vacuo. The residue was purified by silica chromatography to afford the title compound (40 mg, 0.060 mmol, 33% yield). $^1$H NMR (400 MHz, CHLOROFORM-d) (mixture of rotamers) δ ppm 7.4 (d, J=5.31 Hz, 1H), 7.0-7.1 (m, 1H), 6.8-7.0 (m, 3H), 5.0 (d, J=8.79 Hz, 1H), 4.3 (t, J=5.13 Hz, 2H), 4.0 (dd, J=14.38, 7.05 Hz, 3H), 3.7-3.8 (m, 1H), 3.4-3.6 (m, 2H), 3.1-3.2 (m, 2H), 3.0 (d, J=5.86 Hz, 2H), 2.7 (t, J=6.13 Hz, 2H), 2.5 (br. s., 1.5H), 2.4 (br. s., 1.5H), 2.1 (dd, J=5.86, 3.11 Hz, 2H), 1.8-1.9 (m, 6H), 1.1-1.2 (m, 12H). LCMS (ES+) (m/z): 658.54, 660.51 (M+Na).

Step 10

(S)-2-(tert-butoxy)-2-((M)-8-(8-chloro-5-methylchroman-6-yl)-3-(3-fluorobenzoyl)-6,9-dimethyl-2,3,4,5-tetrahydro-1H-benzo[d]azepin-7-yl)acetic Acid

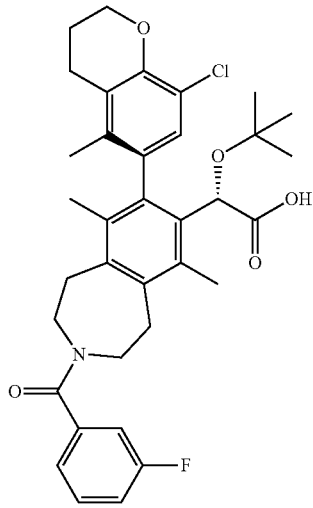

A solution of (S)-ethyl 2-(tert-butoxy)-2-((M)-8-(8-chloro-5-methylchroman-6-yl)-3-(3-fluorobenzoyl)-6,9-dimethyl-2,3,4,5-tetrahydro-1H-benzo[d]azepin-7-yl)acetate (38 mg, 0.060 mmol) and potassium trimethylsilanolate (30.7 mg, 0.239 mmol) in 1,4-dioxane (2 mL) were heated at 100° C. After 1 h, the reaction mixture was allowed to cool to ambient temperature and concentrated in vacuo. The residue was purified by silica chromatography (0-10% MeOH/DCM) to afford the title compound (18 mg, 0.027 mmol, 45% yield) as a white solid. $^1$H NMR (400 MHz, 80° C., DMSO-d$_6$) δ ppm 11.7-12.0 (m, 1H), 7.3-7.5 (m, 1H), 7.1-7.3 (m, 1H), 6.8 (br. s., 3H), 4.9 (s, 1H), 4.2 (t, J=4.94 Hz, 2H), 3.4-3.9 (m, 4H), 2.9-3.1 (m, 4H), 2.7 (t, J=5.95 Hz, 2H), 2.3 (br. s., 3H), 2.0-2.1 (m, 2H), 1.8 (s, 6H), 1.0-1.2 (m, 9H). LCMS (ES+) (m/z): 630.48, 632.49 (M+Na).

Examples 2-4 were made in a similar manner as Example 1.

Example 2: (S)-2-(tert-butoxy)-2-(3-(3-fluorobenzoyl)-8-(4-methoxyphenyl)-6,9-dimethyl-2,3,4,5-tetrahydro-1H-benzo[d]azepin-7-yl)acetic Acid

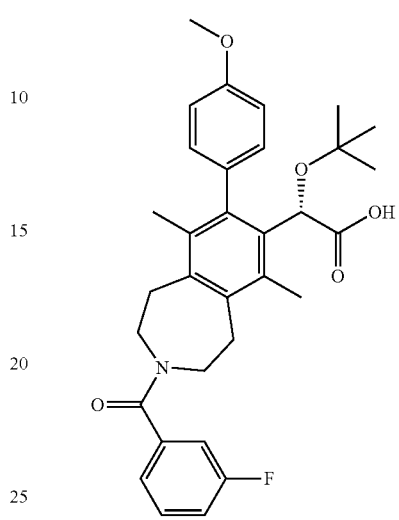

$^1$H NMR (400 MHz, CHLOROFORM-d) (mixture of rotamers) δ ppm 7.4 (br. s., 1H), 7.4 (d, J=7.14 Hz, 1H), 7.0-7.2 (m, 2H), 6.9-7.0 (m, 3H), 6.8 (d, J=7.33 Hz, 1H), 5.2 (s, 1H), 3.9-4.0 (m, 0.5H), 3.8-3.9 (m, 3H), 3.8-3.8 (m, 0.5H), 3.4-3.7 (m, 3H), 3.0-3.3 (m, 2 H), 3.0 (d, J=5.68 Hz, 2H), 2.4 (br. s., 1.5H), 2.2 (br. s., 1.5H), 2.0 (br. s., 1.5H), 1.9 (br. s., 1.5H), 1.0 (s, 9H). LCMS (ES+) (m/z): 534.45 (M+H), 556.45 (M+Na).

Example 3: (S)-2-(tert-butoxy)-2-(3-(3-fluorobenzoyl)-6,9-dimethyl-8-phenyl-2,3,4,5-tetrahydro-1H-benzo[d]azepin-7-yl)acetic Acid

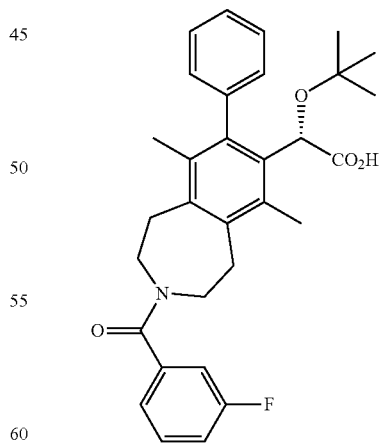

$^1$H NMR (400 MHz, 80° C., DMSO-d$_6$) δ ppm 7.6-7.9 (m, 1H), 7.3-7.5 (m, 5H), 7.2 (d, J=7.14 Hz, 2H), 6.7-6.9 (m, 2H), 4.9 (s, 1H), 3.3-3.9 (m, 4H), 3.1 (s, 4H), 2.3 (br. s., 3H), 1.8 (br. s., 3H), 0.9 (s, 9H). LCMS (ES+) (m/z): 504.41 (M+H), 526.40 (M+Na).

Example 4: (S)-2-(tert-butoxy)-2-(3-(3-fluorobenzoyl)-6,9-dimethyl-8-(p-tolyl)-2,3,4,5-tetrahydro-1H-benzo[d]azepin-7-yl)acetic Acid
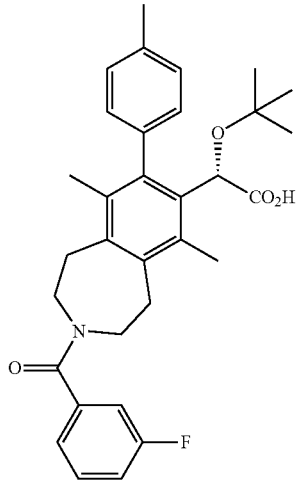 [SMILES: Cc1ccc(-c2c(C)c3c(c(C)c2[C@H](OC(C)(C)C)C(=O)O)CCN(C(=O)c2cccc(F)c2)CC3)cc1]
$^1$H NMR (400 MHz, METHANOL-$d_4$) (mixture of rotamers) δ ppm 7.49-7.21 (m, 4H), 7.19-7.03 (m, 2H), 6.88-6.75 (m, 1H), 6.69-6.51 (m, 1H), 5.13-5.04 (m, 1H), 4.10-3.92 (m, 1H), 3.86-3.67 (m, 1H), 3.60-3.38 (m, 2H), 3.27-3.07 (m, 2H), 3.05-2.89 (m, 2H), 2.49-2.18 (m, 6H), 2.06-1.66 (m, 3H), 0.93 (br. s, 9H); LCMS (m/z) ES$^+$=518.48 (M+1).
Scheme 2
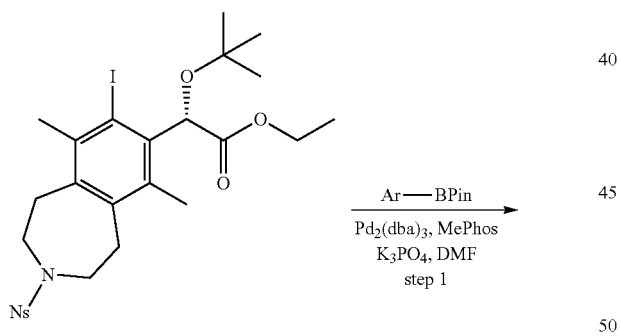
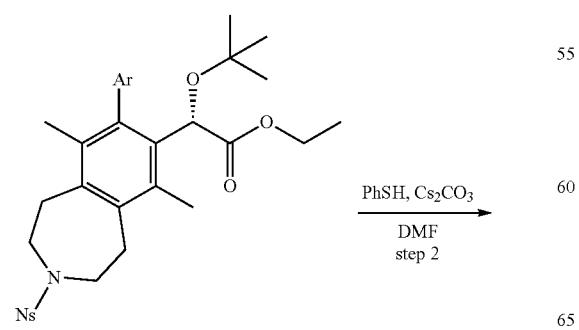
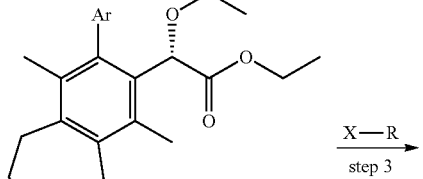
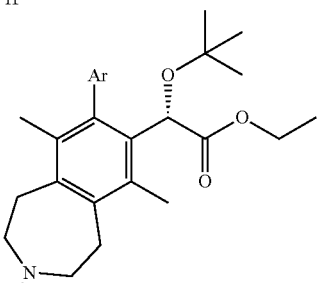
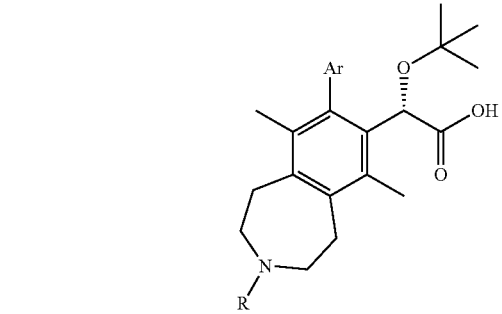
Example 5: (2S)-2-(tert-butoxy)-2-((M)-8-(8-fluoro-5-methylchroman-6-yl)-3-(3-fluorobenzoyl)-6,9-dimethyl-2,3,4,5-tetrahydro-1H-benzo[d]azepin-7-yl)acetic Acid
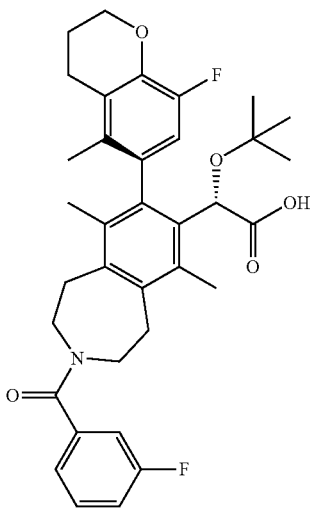

Step 1

(2S)-Ethyl 2-(tert-butoxy)-2-((M)-8-(8-fluoro-5-methylchroman-6-yl)-6,9-dimethyl-3-(2-nitrophenyl)sulfonyl)-2,3,4,5-tetrahydro-1H-benzo[d]azepin-7-yl)acetate

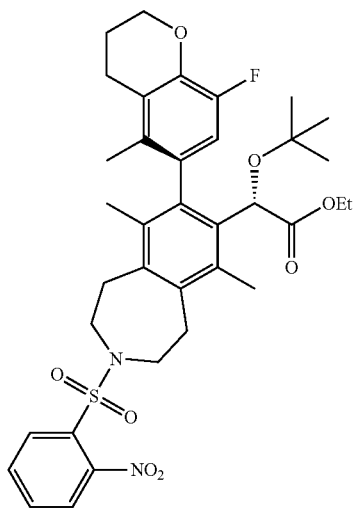

A solution of (S)-Ethyl 2-(tert-butoxy)-2-(8-iodo-6,9-dimethyl-3-((2-nitrophenyl)sulfonyl)-2,3,4,5-tetrahydro-1H-benzo[d]azepin-7-yl)acetate (1 g, 1.552 mmol), 2-(8-fluoro-5-methylchroman-6-yl)-4,4,5,5-tetramethyl-1,3,2-dioxaborolane (0.725 g, 2.482 mmol), $K_3PO_4$ (0.988 g, 4.65 mmol), and MePhos (0.170 g, 0.465 mmol) in N,N-Dimethylformamide (15 mL) was degassed with $N_2$ for 5 min, treated with $Pd_2(dba)_3$ (0.426 g, 0.465 mmol), and immersed in 80° C. oil bath. After 50 min, the reaction mixture was cooled to ambient temperature, diluted with water and filtered through a pad of Celite. The filtrate was extracted with EtOAc, washed with water, brine, dried over $Na_2SO_4$, filtered, and concentrated in vacuo. The residue was purified by silica gel chromatography (0-60% EtOAc/Hexane) to afford the title compound as a brown solid. LCMS (m/z) ES+=705.70 (M+Na).

Step 2

(2S)-ethyl 2-(tert-butoxy)-2-((M)-8-(8-fluoro-5-methylchroman-6-yl)-6,9-dimethyl-2,3,4,5-tetrahydro-1H-benzo[d]azepin-7-yl)acetate

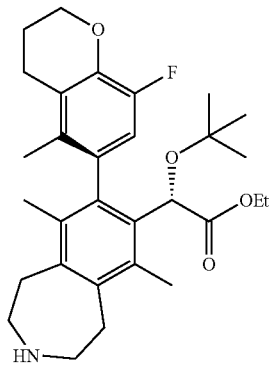

A solution of (2S)-Ethyl 2-(tert-butoxy)-2-(8-(8-fluoro-5-methylchroman-6-yl)-6,9-dimethyl-3-((2-nitrophenyl)sulfonyl)-2,3,4,5-tetrahydro-1H-benzo[d]azepin-7-yl)acetate (580 mg, 0.849 mmol) and $Cs_2CO_3$ (1107 mg, 3.40 mmol) in N,N-Dimethylformamide (10 mL) was treated with thiophenol (0.350 mL, 3.40 mmol). After 1.5 h, the mixture was diluted with water, extracted with EtOAc, washed with water, brine, dried over $Na_2SO_4$, filtered, and concentrated in vacuo. The residue was purified by silica gel chromatography (0-20% MeOH/DCM) to afford the title compound. $^1$H NMR (400 MHz, CHLOROFORM-d) δ ppm 6.70 (d, J=11.5 Hz, 1H), 4.94 (s, 1H), 4.28 (t, J=5.1 Hz, 2H), 4.11-3.98 (m, 2H), 3.08-2.87 (m, 8H), 2.78-2.64 (m, 2H), 2.42 (s, 3H), 2.21-2.06 (m, 2H), 1.84-1.79 (m, 6H), 1.14 (t, J=7.1 Hz, 3H), 1.10 (s, 9H); LCMS (m/z) ES+=498.58 (M+1).

Step 3

(S)-Ethyl 2-(tert-butoxy)-2-((M)-8-(8-fluoro-5-methylchroman-6-yl)-3-(3-fluorobenzoyl)-6,9-dimethyl-2,3,4,5-tetrahydro-1H-benzo[d]azepin-7-yl)acetate

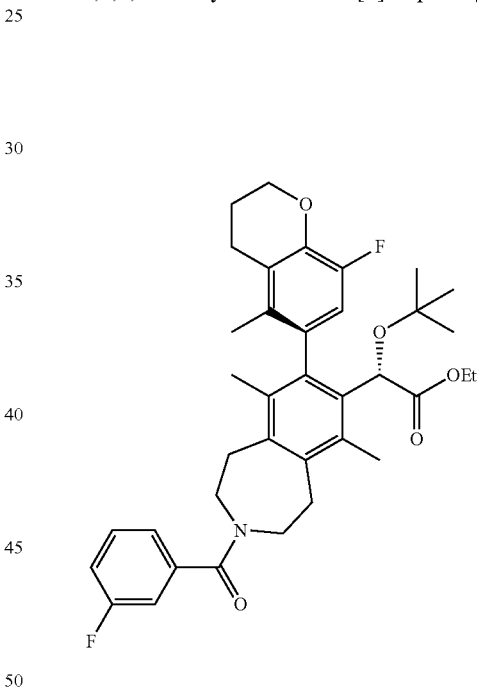

A solution of (2S)-Ethyl 2-(tert-butoxy)-2-((M)-8-(8-fluoro-5-methylchroman-6-yl)-6,9-dimethyl-2,3,4,5-tetrahydro-1H-benzo[d]azepin-7-yl)acetate (40 mg, 0.080 mmol) in ethyl acetate (1.6 mL) was treated with 3-fluorobenzoic acid (16.89 mg, 0.121 mmol), $Et_3N$ (0.034 mL, 0.241 mmol), 1-propanephosphonic acid cyclic anhydride (0.120 mL, 0.201 mmol, 50 wt. % solution in ethyl acetate), and stirred at ambient temperature. After 70 min, the reaction was diluted with sat. $NaHCO_3$, extracted with EtOAc, washed with Brine, dried over $Na_2SO_4$, filtered, and concentrated in vacuo to afford the title compound (47.6 mg, 0.077 mmol, 96% yield) as a light yellow oil. LCMS (m/z) ES+=642.71 (M+Na).

Step 4

(2S)-2-(tert-butoxy)-2-((M)-8-(8-fluoro-5-methyl-chroman-6-yl)-3-(3-fluorobenzoyl)-6,9-dimethyl-2,3,4,5-tetrahydro-1H-benzo[d]azepin-7-yl)acetic Acid A solution of (2S)-Ethyl 2-(tert-butoxy)-2-((M)-8-(8-fluoro-5-methylchroman-6-yl)-3-(3-fluorobenzoyl)-6,9-dimethyl-2,3,4,5-tetrahydro-1H-benzo[d]azepin-7-yl)acetate (47.6 mg, 0.077 mmol, 96% yield) in 1,4-Dioxane (1.5 mL) was treated with KOTMS (41.2 mg, 0.322 mmol) and heated to 100° C. After 4 h, the reaction mixture was treated with additional KOTMS (20 mg) and stirring continued at 100° C. After 30 min, the reaction mixture was cooled to ambient temperature and partitioned between 1N HCl and EtOAc. The organic layer was washed with brine, dried over $Na_2SO_4$, filtered, and concentrated in vacuo. The residue was purified by reverse phase HPLC (30-100% MeCN/$H_2O$-0.1% TFA) to afford the title compound (24.1 mg, 0.037 mmol, 45.6% yield) as white solid. $^1$H NMR (400 MHz, METHANOL-d4) (mixture of rotamers and atropisomers) δ ppm 7.50-7.27 (m, 1H), 7.22-7.04 (m, 1H), 6.94-6.52 (m, 3H), 5.13-4.97 (m, 1H), 4.23 (t, J=4.9 Hz, 2H), 4.12-3.62 (m, 2H), 3.59-3.40 (m, 2H), 3.25-3.07 (m, 2H), 3.01 (t, J=6.2 Hz, 2H), 2.73 (t, J=6.3 Hz, 2H), 2.52-2.21 (m, 3H), 2.19-2.05 (m, 2H), 1.99-1.65 (m, 6H), 1.18-0.94 (m, 9H); LCMS (m/z) ES+=614.45 (M+23), ES−=590.39 (M−1).

Examples 6-14 were made in a similar manner as Example 5.

Example 6: (S)-2-(tert-butoxy)-2-((M)-3-(3,3-dimethylbutanoyl)-8-(8-fluoro-5-methylchroman-6-yl)-6,9-dimethyl-2,3,4,5-tetrahydro-1H-benzo[d]azepin-7-yl)acetic Acid

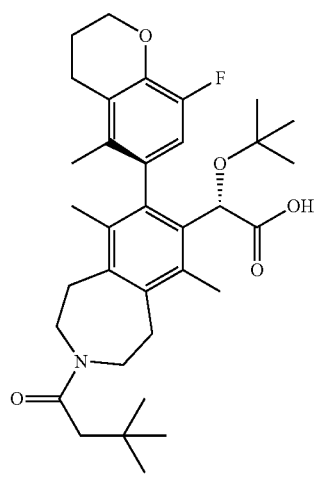

$^1$H NMR (400 MHz, METHANOL-$d_4$) (mixture of rotamers) δ ppm 6.95 (d, J=12.2 Hz, 0.1H), 6.57 (d, J=11.1 Hz, 0.9H), 5.04-4.92 (m, 1H), 4.22 (t, J=4.7 Hz, 2H), 3.89-3.60 (m, 4H), 3.18-2.97 (m, 4H), 2.72 (t, J=6.0 Hz, 2H), 2.50-2.35 (m, 3H), 2.27-1.98 (m, 4H), 1.93-1.71 (m, 6H), 1.15-0.84 (m, 18H); LCMS (m/z) ES+=568.69 (M+1), ES−=566.69 (M−1).

Example 7: (S)-2-(tert-butoxy)-2-((M)-3-(5-fluoro-2-methoxybenzoyl)-8-(8-fluoro-5-methylchroman-6-yl)-6,9-dimethyl-2,3,4,5-tetrahydro-1H-benzo[d]azepin-7-yl)acetic Acid

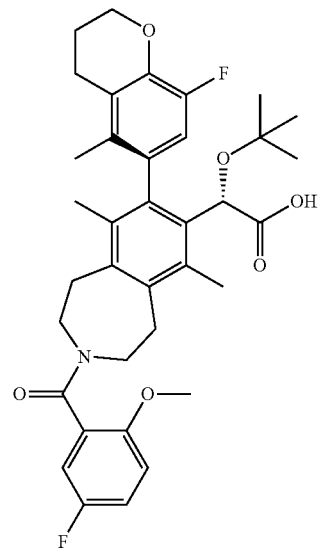

$^1$H NMR (400 MHz, CHLOROFORM-d) (mixture of rotamers) δ ppm 7.11-6.95 (m, 1H), 6.93-6.37 (m, 3H), 5.26-4.96 (m, 1H), 4.37-3.93 (m, 3H), 3.91-3.58 (m, 4H), 3.52-2.87 (m, 6H), 2.79-2.59 (m, 2H), 2.44-2.19 (m, 3H), 2.18-2.05 (m, 2H), 1.93-1.73 (m, 6H), 1.20-0.97 (m, 9H); LCMS (m/z) ES+=622.75 (M+1), ES−=620.67 M+1).

Example 8: (S)-2-(tert-butoxy)-2-((M)-8-(8-fluoro-5-methylchroman-6-yl)-3-(2-methoxy-5-methylbenzoyl)-6,9-dimethyl-2,3,4,5-tetrahydro-1H-benzo[d]azepin-7-yl)acetic Acid

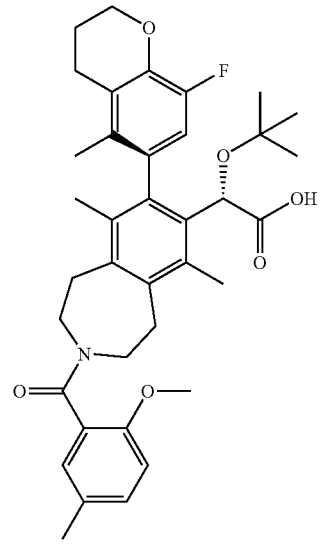

$^1$H NMR (400 MHz, CHLOROFORM-d) (mixture of rotamers) δ ppm 7.20-7.07 (m, 1H), 7.03-6.64 (m, 3H), 5.15-5.03 (m, 1H), 4.34-4.19 (m, 2H), 4.15-3.69 (m, 5H), 3.57-2.84 (m, 6H), 2.80-2.53 (m, 2H), 2.43-2.18 (m, 6H), 2.16-2.04 (m, 2H), 1.94-1.73 (m, 6H), 1.21-0.97 (m, 9H); LCMS (m/z) ES$^+$=618.75 (M+1), ES$^-$=616.71 (M+1).

Example 9: (S)-2-(tert-butoxy)-2-((M)-8-(8-fluoro-5-methylchroman-6-yl)-3-(4-methoxy-3-methylbenzoyl)-6,9-dimethyl-2,3,4,5-tetrahydro-1H-benzo[d]azepin-7-yl)acetic Acid

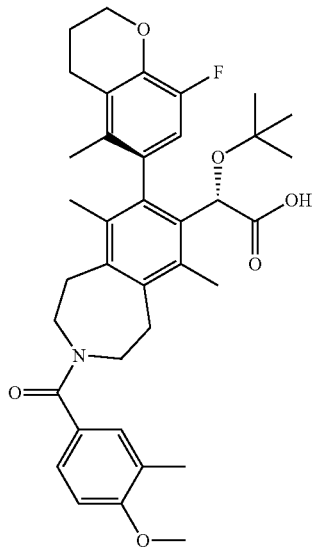

$^1$H NMR (400 MHz, METHANOL-d$_4$) (mixture of rotamers) δ ppm 7.13-6.54 (m, 4H), 5.11-4.97 (m, 1H), 4.30-4.14 (m, 2H), 4.08-3.78 (m, 4H), 3.74-3.44 (m, 3H), 3.25-2.89 (m, 4H), 2.79-2.62 (m, 2H), 2.55-2.24 (m, 3H), 2.23-2.01 (m, 5H), 1.99-1.64 (m, 6H), 1.16-0.91 (m, 9H); LCMS (m/z) ES$^+$=618.64 (M+1), ES$^-$=616.68 (M-1).

Example 10: (S)-2-(tert-butoxy)-2-((M)-3-(3-fluoro-2-methoxybenzoyl)-8-(8-fluoro-5-methylchroman-6-yl)-6,9-dimethyl-2,3,4,5-tetrahydro-1H-benzo[d]azepin-7-yl)acetic Acid

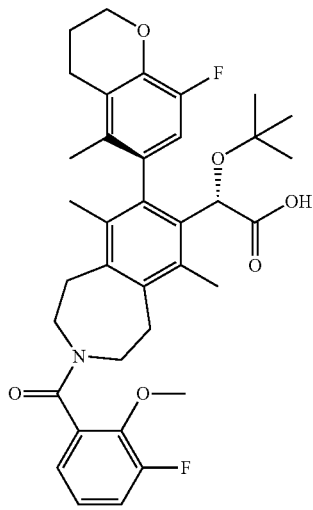

$^1$H NMR (400 MHz, METHANOL-d$_4$) δ ppm 7.32-6.89 (m, 2H), 6.73-6.50 (m, 1H), 6.42-6.06 (m, 1H), 5.17-4.97 (m, 1H), 4.57-4.13 (m, 3H), 3.86 (s, 3H), 3.72-3.19 (m, 4H), 3.15-2.85 (m, 3H), 2.79-2.63 (m, 2H), 2.55-2.20 (m, 3H), 2.17-2.02 (m, 2H), 2.00-1.62 (m, 6H), 1.17-0.92 (m, 9H); LCMS (m/z) ES$^+$=622.65 (M+1), ES$^-$=620.69 (M-1).

Example 11: (S)-2-(tert-butoxy)-2-((M)-3-(2,3-dihydrobenzofuran-7-carbonyl)-8-(8-fluoro-5-methylchroman-6-yl)-6,9-dimethyl-2,3,4,5-tetrahydro-1H-benzo[d]azepin-7-yl)acetic Acid

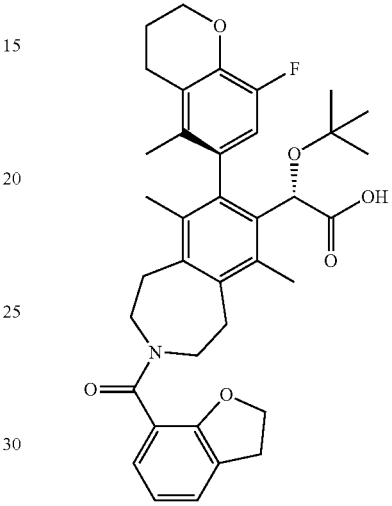

$^1$H NMR (400 MHz, CHLOROFORM-d) (mixture of rotamers) δ ppm 7.21 (d, J=7.0 Hz, 1H), 6.95-6.63 (m, 3H), 5.09 (br. s., 1H), 4.61 (t, J=8.7 Hz, 2H), 4.32-4.20 (m, 2H), 4.15-3.69 (m, 2H), 3.60-3.41 (m, 2H), 3.23 (t, J=8.6 Hz, 2H), 3.19-3.03 (m, 2H), 3.02-2.92 (m, 2H), 2.79-2.57 (m, 2H), 2.41-2.17 (m, 3H), 2.16-2.06 (m, 2H), 1.96-1.73 (m, 6H), 1.19-0.98 (m, 9H); LCMS (m/z) ES$^+$=616.72 (M+1), ES$^-$=614.67 (M+1).

Example 12: (S)-2-(tert-butoxy)-2-((M)-3-(cyclohexanecarbonyl)-8-(8-fluoro-5-methylchroman-6-yl)-6,9-dimethyl-2,3,4,5-tetrahydro-1H-benzo[d]azepin-7-yl)acetic Acid

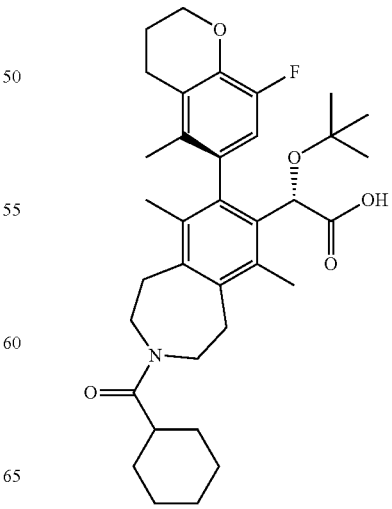

$^{1}$H NMR (400 MHz, METHANOL-d$_{4}$) (mixture of rotamers) δ ppm 7.00-6.39 (m, 1H), 5.03-4.92 (m, 1H), 4.32-4.11 (m, 2H), 3.83-3.57 (m, 4H), 3.20-2.95 (m, 4H), 2.79-2.63 (m, 2H), 2.52-2.32 (m, 4H), 2.10 (br. s., 2H), 1.93-1.76 (m, 6H), 1.75-1.59 (m, 3H), 1.50-1.11 (m, 7H), 1.10-0.90 (m, 9H); LCMS (m/z) ES$^{+}$=580.46 (M+1), ES$^{-}$=578.40 (M−1).

Example 13: (S)-2-(tert-butoxy)-2-((M)-3-(4-fluoro-3-methoxybenzoyl)-8-(8-fluoro-5-methylchroman-6-yl)-6,9-dimethyl-2,3,4,5-tetrahydro-1H-benzo[d]azepin-7-yl)acetic Acid

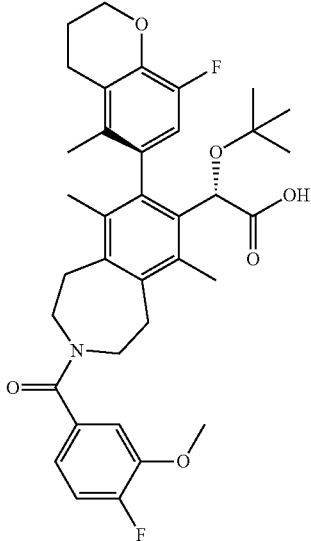

$^{1}$H NMR (400 MHz, METHANOL-d$_{4}$) (mixture of rotamers) δ ppm 7.18-7.00 (m, 1H), 6.97-6.78 (m, 1H), 6.71-6.18 (m, 2H), 5.14-4.97 (m, 1H), 4.23 (t, J=4.6 Hz, 2H), 4.17-4.02 (m, 1H), 3.97-3.45 (m, 6H), 3.25-2.89 (m, 4H), 2.72 (t, J=5.9 Hz, 2H), 2.58-2.23 (m, 3H), 2.18-2.02 (m, 2H), 1.99-1.63 (m, 6H), 1.19-0.91 (m, 9H); LCMS (m/z) ES$^{-}$=620.67 (M−1).

Example 14: (S)-2-(tert-butoxy)-2-((M)-8-(8-fluoro-5-methylchroman-6-yl)-6,9-dimethyl-3-(2-oxo-2-(piperidin-1-yl)acetyl)-2,3,4,5-tetrahydro-1H-benzo[d]azepin-7-yl)acetic Acid

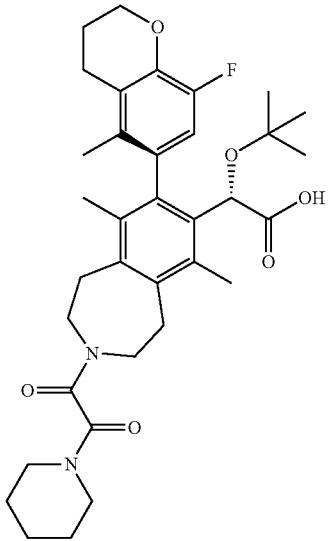

$^{1}$H NMR (400 MHz, METHANOL-d$_{4}$) (mixture of rotamers) δ ppm 6.62-6.41 (m, 1H), 5.02-4.94 (m, 1H), 4.23 (t, J=5.0 Hz, 2H), 3.95-3.68 (m, 2H), 3.67-3.39 (m, 4H), 3.25-2.97 (m, 5H), 2.88-2.62 (m, 3H), 2.51-2.37 (m, 3H), 2.19-2.03 (m, 2H), 1.93-1.75 (m, 6H), 1.74-1.37 (m, 6H), 1.16-0.91 (m, 9H); LCMS (m/z) ES$^{-}$=607.73 (M−1).

Example 15: (S)-2-(tert-butoxy)-2-((M)-8-(8-fluoro-5-methylchroman-6-yl)-3-(3-fluorobenzyl)-6,9-dimethyl-2,3,4,5-tetrahydro-1H-benzo[d]azepin-7-yl) acetic Acid Step 1

(2S)-ethyl 2-(tert-butoxy)-2-((M)-8-(8-fluoro-5-methylchroman-6-yl)-3-(3-fluorobenzyl)-6,9-dimethyl-2,3,4,5-tetrahydro-1H-benzo[d]azepin-7-yl) acetate A solution of (2S)-Ethyl 2-(tert-butoxy)-2-((M)-8-(8-fluoro-5-methylchroman-6-yl)-6,9-dimethyl-2,3,4,5-tetrahydro-1H-benzo[d]azepin-7-yl)acetate (30 mg, 0.060 mmol) in 1,2-dichloroethane (1 mL) was treated with 3-fluorobenzaldehyde (9.59 µl, 0.090 mmol). After 10 min, sodium triacetoxyborohydride (20.44 mg, 0.096 mmol) was added and the reaction stirred at ambient temperature. After 1.5 h, the reaction mixture was charged with additional 3-fluorobenzaldehyde (9.59 µl, 0.090 mmol), sodium triacetoxyborohydride (20.44 mg, 0.096 mmol). After 1 h, the reaction mixture was diluted with sat. NaHCO$_{3}$, extracted with DCM, washed with brine, dried over Na$_{2}$SO$_{4}$, filtered, and concentrated in vacuo to afford (S)-ethyl 2-(tert-butoxy)-2-((M)-8-(8-fluoro-5-methylchroman-6-yl)-3-(3-fluorobenzyl)-6,9-dimethyl-2,3,4,5-tetrahydro-1H-benzo[d]azepin-7-yl)acetate (44 mg, 0.073 mmol, 120% yield) as light yellow oil. LCMS (m/z) ES+=606.73 (M+1).

Step 2

(S)-2-(tert-butoxy)-2-((M)-8-(8-fluoro-5-methyl-chroman-6-yl)-3-(3-fluorobenzyl)-6,9-dimethyl-2,3,4,5-tetrahydro-1H-benzo[d]azepin-7-yl)acetic Acid The title compound was made in a similar manner as in Example 5, Step 4. $^1$H NMR (400 MHz, METHANOL-d$_4$) δ ppm 7.60-7.49 (m, 1H), 7.41-7.22 (m, 3H), 6.97-6.48 (m, 1H), 5.05-4.95 (m, 1H), 4.38 (s, 2H), 4.23 (t, J=5.1 Hz, 2H), 3.84-3.62 (m, 2H), 3.56-3.36 (m, 2H), 3.21-2.94 (m, 4H), 2.73 (t, J=6.1 Hz, 2H), 2.50-2.37 (m, 3H), 2.20-2.02 (m, 2H), 1.95-1.85 (m, 3H), 1.84-1.70 (m, 3H), 1.07 (s, 8H), 0.95 (s, 1H); LCMS (m/z) ES$^+$=578.78 (M+1), ES$^-$=576.66 (M−1).

Example 16: (2S)-2-(tert-butoxy)-2-((M)-3-(2-cyclohexylethyl)-8-(8-fluoro-5-methylchroman-6-yl)-6,9-dimethyl-2,3,4,5-tetrahydro-1H-benzo[d]azepin-7-yl)acetic Acid

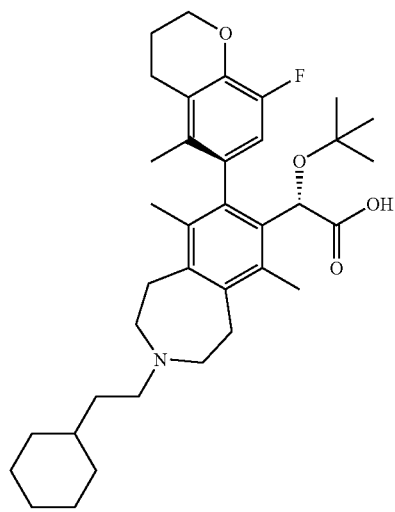

$^1$H NMR (400 MHz, METHANOL-d$_4$) δ ppm 6.67-6.42 (m, 1H), 4.99 (s, 1H), 4.23 (t, J=5.1 Hz, 2H), 3.86-3.70 (m, 2H), 3.56-3.37 (m, 2H), 3.26-2.93 (m, 6H), 2.73 (t, J=6.5 Hz, 2H), 2.49-2.40 (m, 3H), 2.18-2.05 (m, 2H), 1.95-1.85 (m, 3H), 1.85-1.16 (m, 14H), 1.11-0.92 (m, 11H); LCMS (m/z) ES$^+$=580.48 (M+1), ES$^-$=578.77 (M−1).

Example 17: (S)-2-(tert-butoxy)-2-((M)-3-(cyclohexylmethyl)-8-(8-fluoro-5-methylchroman-6-yl)-6,9-dimethyl-2,3,4,5-tetrahydro-1H-benzo[d]azepin-7-yl)acetic Acid

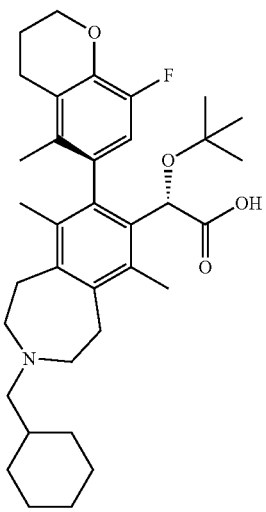

$^1$H NMR (400 MHz, METHANOL-d$_4$) δ ppm 7.00-6.38 (m, 1H), 5.07-4.95 (m, 1H), 4.23 (t, J=4.9 Hz, 2H), 3.87-3.63 (m, 2H), 3.54-3.37 (m, 2H), 3.21-3.08 (m, 2H), 3.07-2.91 (m, 4H), 2.73 (t, J=5.5 Hz, 2H), 2.50-2.37 (m, 3H), 2.21-2.04 (m, 2H), 2.00-1.67 (m, 12H), 1.49-1.18 (m, 3H), 1.17-0.89 (m, 11H); LCMS (m/z) ES$^+$=566.50 (M+1).

Example 18: (2S)-2-(tert-butoxy)-2-((M)-3-cyclohexyl-8-(8-fluoro-5-methylchroman-6-yl)-6,9-dimethyl-2,3,4,5-tetrahydro-1H-benzo[d]azepin-7-yl)acetic Acid

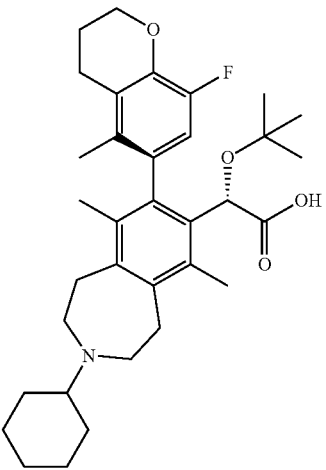

$^1$H NMR (400 MHz, METHANOL-d$_4$) δ ppm 6.99-6.38 (m, 1H), 5.12-4.96 (m, 1H), 4.41-4.06 (m, 2H), 3.89-3.62 (m, 2H), 3.61-3.39 (m, 2H), 3.23-2.95 (m, 4H), 2.84-2.59 (m, 2H), 2.55-2.32 (m, 3H), 2.23-2.01 (m, 4H), 2.00-1.63 (m, 9H), 1.63-1.48 (m, 2H), 1.47-1.28 (m, 3H), 1.27-1.15 (m, 1H), 1.14-0.87 (m, 9H); LCMS (m/z) ES$^+$=552.47 (M+1), ES$^-$=550.46 (M+1).

Example 19: (2S)-2-(tert-butoxy)-2-((M)-8-(8-fluoro-5-methylchroman-6-yl)-6,9-dimethyl-3-phenyl-2,3,4,5-tetrahydro-1H-benzo[d]azepin-7-yl)acetic Acid

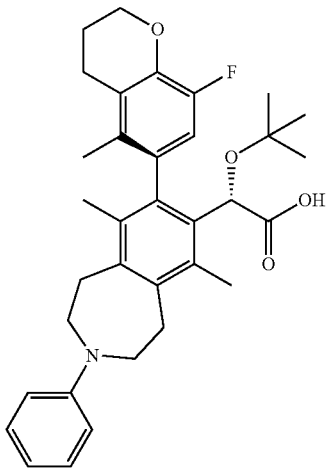

Step 1

(2S)-ethyl 2-(tert-butoxy)-2-((M)-8-(8-fluoro-5-methylchroman-6-yl)-6,9-dimethyl-3-phenyl-2,3,4,5-tetrahydro-1H-benzo[d]azepin-7-yl)acetate A solution of (2S)-ethyl 2-(tert-butoxy)-2-((M)-8-(8-fluoro-5-methylchroman-6-yl)-6,9-dimethyl-2,3,4,5-tetrahydro-1H-benzo[d]azepin-7-yl)acetate (35 mg, 0.070 mmol) in tetrahydrofuran (2 mL) was treated with iodobenzene (0.024 mL, 0.211 mmol) and RuPhos Pd G1 Methyl-t-Butyl Ether Adduct (5.74 mg, 7.03 µmol). After 10 min, the reaction mixture was treated dropwise with LiHMDS (0.176 mL, 0.176 mmol). After 3 h, the reaction mixture was charged with additional iodobenzene (25 uL), Ruphos palladacycle (6 mg), and LiHMDS (180 uL). After 18 h., the reaction mixture was cooled to 0° C., and quenched with sat. aqueous $NH_4Cl$, extracted with EtOAc, washed with brine, dried over $Na_2SO_4$, filtered, and concentrated in vacuo. The residue was purified by silica gel chromatography (0-40% EtOAc/Hexane) to afford the title compound (31.2 mg, 0.054 mmol, 77% yield) as a yellow oil. LCMS (m/z) ES+=574.73 (M+1).

Step 2

(2S)-2-(tert-butoxy)-2-((M)-8-(8-fluoro-5-methylchroman-6-yl)-6,9-dimethyl-3-phenyl-2,3,4,5-tetrahydro-1H-benzo[d]azepin-7-yl)acetic Acid The title compound was made in a similar manner as in Example 5, Step 4. $^1$H NMR (400 MHz, METHANOL-$d_4$) δ ppm 7.67-7.38 (m, 5H), 7.03-6.47 (m, 1H), 5.06-4.97 (m, 1H), 4.32-4.15 (m, 2H), 3.89-3.68 (m, 4H), 3.50-3.36 (m, 4H), 2.80-2.67 (m, 2H), 2.55-2.41 (m, 3H), 2.20-2.05 (m, 2H), 1.98-1.75 (m, 6H), 1.09 (br. s., 8.2H), 0.96 (br. s., 0.8H); LCMS (m/z) ES+=546.48 (M+1), ES−=544.65 (M−1).

Example 20: (2S)-2-(tert-butoxy)-2-((M)-3-(cyclohexylsulfonyl)-8-(8-fluoro-5-methylchroman-6-yl)-6,9-dimethyl-2,3,4,5-tetrahydro-1H-benzo[d]azepin-7-yl)acetic Acid

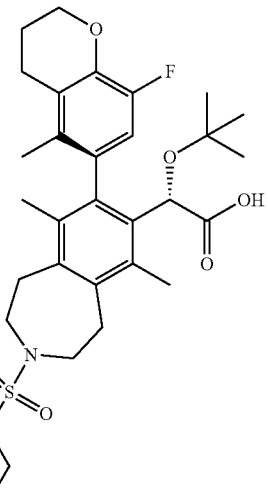

Step 1

(2S)-ethyl 2-(tert-butoxy)-2-((M)-3-(cyclohexylsulfonyl)-8-(8-fluoro-5-methylchroman-6-yl)-6,9-dimethyl-2,3,4,5-tetrahydro-1H-benzo[d]azepin-7-yl)acetate A solution of (2S)-ethyl 2-(tert-butoxy)-2-((M)-8-(8-fluoro-5-methylchroman-6-yl)-6,9-dimethyl-2,3,4,5-tetrahydro-1H-benzo[d]azepin-7-yl)acetate (35 mg, 0.070 mmol) in dichloromethane (1.4 mL) was treated with $Et_3N$ (0.029 mL, 0.211 mmol), cyclohexanesulfonyl chloride (0.015 mL, 0.105 mmol). After 2 h, the reaction mixture was treated with additional $Et_3N$ (50 uL), and cyclohexanesulfonyl chloride (30 uL). After 18 h, the reaction mixture was diluted with sat. $NaHCO_3$, extracted with DCM, washed with brine, dried over $Na_2SO_4$, filtered, and concentrated in vacuo. The residue was purified by silica gel chromatography (0-70% EtOAc/Hexane) to afford the title compound (14.6 mg, 0.023 mmol, 32.2% yield) as a colorless oil. LCMS (m/z) ES+=666.72 (M+23).

Step 2

(2S)-2-(tert-butoxy)-2-((M)-3-(cyclohexylsulfonyl)-8-(8-fluoro-5-methylchroman-6-yl)-6,9-dimethyl-2,3,4,5-tetrahydro-1H-benzo[d]azepin-7-yl)acetic Acid The title compound was made in a similar manner as in Example 5, Step 4. $^1$H NMR (400 MHz, METHANOL-$d_4$) δ ppm 7.10-6.49 (m, 1H), 5.02-4.94 (m, 1H), 4.22 (t, J=5.1 Hz, 2H), 3.60-3.38 (m, 4H), 3.22-3.02 (m, 4H), 2.99-2.87 (m, 1H), 2.72 (t, J=6.2 Hz, 2H), 2.47-2.36 (m, 3H), 2.18-2.05 (m, 2H), 2.04-1.91 (m, 2H), 1.87-1.76 (m, 7H), 1.71-1.60 (m, 1H), 1.45-1.13 (m, 6H), 1.12-0.90 (m, 9H); LCMS (m/z) ES−=614.69 (M−1).

Example 21: (2S)-2-(tert-butoxy)-2-((M)-8-(8-fluoro-5-methylchroman-6-yl)-6,9-dimethyl-3-(piperidin-1-ylsulfonyl)-2,3,4,5-tetrahydro-1H-benzo[d]azepin-7-yl)acetic Acid

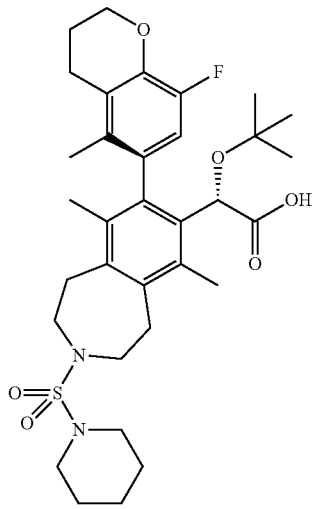

Step 1

(2S)-ethyl 2-(tert-butoxy)-2-((M)-8-(8-fluoro-5-methylchroman-6-yl)-6,9-dimethyl-3-(piperidin-1-ylsulfonyl)-2,3,4,5-tetrahydro-1H-benzo[d]azepin-7-yl)acetate A solution of (2S)-ethyl 2-(tert-butoxy)-2-((M)-8-(8-fluoro-5-methylchroman-6-yl)-6,9-dimethyl-2,3,4,5-tetrahydro-1H-benzo[d]azepin-7-yl)acetate (45 mg, 0.090 mmol) in dichloromethane (1.8 mL) was treated with $Et_3N$ (0.038 mL, 0.271 mmol), and piperidine-1-sulfonyl chloride (0.019 mL, 0.136 mmol). After 1.5 h, the reaction mixture was treated with additional $Et_3N$ (20 uL), piperidine-1-sulfonyl chloride (10 uL). After 2 h, the reaction mixture was diluted with sat. $NaHCO_3$, extracted with DCM, washed with brine, dried over $Na_2SO_4$, filtered, and concentrated in vacuo to afford the title compound (137.1 mg, 0.213 mmol) as light yellow oil. LCMS (m/z) ES+=667.52 (M+Na).

Step 2

(2S)-2-(tert-butoxy)-2-((M)-8-(8-fluoro-5-methyl-chroman-6-yl)-6,9-dimethyl-3-(piperidin-1-ylsulfonyl)-2,3,4,5-tetrahydro-1H-benzo[d]azepin-7-yl)acetic Acid The title compound was made in a similar manner as in Example 5, Step 4. $^1$H NMR (400 MHz, CHLOROFORM-d) δ ppm 6.70 (d, J=11.1 Hz, 1H), 5.09 (br. s., 1H), 4.27 (t, J=5.0 Hz, 2H), 3.46 (br. s., 4H), 3.10 (br. s., 8H), 2.81-2.56 (m, 2H), 2.31 (s, 3H), 2.19-2.06 (m, 2H), 1.93-1.79 (m, 6H), 1.66-1.43 (m, 6H), 1.21-0.98 (m, 9H); LCMS (m/z) ES$^+$=617.47 (M+1), ES$^-$=615.38 (M-1).

Example 22: (2S)-2-(tert-butoxy)-2-((M)-8-(8-fluoro-5-methylchroman-6-yl)-6,9-dimethyl-3-(piperidine-1-carbonyl)-2,3,4,5-tetrahydro-1H-benzo[d]azepin-7-yl)acetic Acid

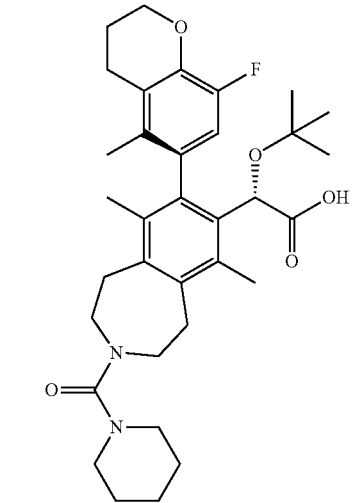

Step 1

(2S)-ethyl 2-(tert-butoxy)-2-((M)-8-(8-fluoro-5-methylchroman-6-yl)-6,9-dimethyl-3-(piperidine-1-carbonyl)-2,3,4,5-tetrahydro-1H-benzo[d]azepin-7-yl)acetate An ice cold solution of phosgene (20% in toluene) (0.120 mL, 0.226 mmol) in tetrahydrofuran (0.5 mL) was treated dropwise to a solution of (2S)-ethyl 2-(tert-butoxy)-2-((M)-8-(8-fluoro-5-methylchroman-6-yl)-6,9-dimethyl-2,3,4,5-tetrahydro-1H-benzo[d]azepin-7-yl)acetate (45 mg, 0.090 mmol) in tetrahydrofuran (1 mL). After 40 min, the reaction mixture was treated with additional phosgene (100 uL). After 1.5 h, the reaction mixture was concentrated in vacuo and the residue dissolved in THF (1 mL). The reaction mixture was cooled to 0° C. and treated with pyridine (8.04 μl, 0.099 mmol) and piperidine (0.045 mL, 0.452 mmol). After 1 h, the reaction mixture was diluted with ice water, extracted with EtOAc, washed with 1N HCl, brine, dried over $Na_2SO_4$, filtered, and concentrated in vacuo to afford the title compound (53.9 mg, 0.089 mmol, 98% yield) as a colorless oil. LCMS (m/z) ES+=631.5 (M+1).

Step 2

(2S)-2-(tert-butoxy)-2-((M)-8-(8-fluoro-5-methyl-chroman-6-yl)-6,9-dimethyl-3-(piperidine-1-carbonyl)-2,3,4,5-tetrahydro-1H-benzo[d]azepin-7-yl)acetic Acid The title compound was made in a similar manner as in Example 5, Step 4. $^1$H NMR (400 MHz, CHLOROFORM-d) δ ppm 6.71 (d, J=11.3 Hz, 1H), 5.07 (br. s., 1H), 4.27 (t, J=5.0 Hz, 2H), 3.56-3.33 (m, 4H), 3.16-2.96 (m, 8H), 2.79-2.58 (m, 2H), 2.31 (s, 3H), 2.18-2.06 (m, 2H), 1.92-1.80 (m, 6H), 1.53 (br. s., 6H), 1.18-0.97 (m, 9H); LCMS (m/z) ES$^+$=581.49 (M+1), ES$^-$=579.43 (M-1).

Anti-HIV Activity

MT4 Assay

Antiviral HIV activity and cytotoxicity values for compounds of the invention from Table 1 were measured in parallel in the HTLV-1 transformed cell line MT-4 based on the method previously described (Hazen et al., 2007, In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV (Hazen et al., "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV", Antimicrob. Agents Chemother. 2007, 51: 3147-3154; and Pauwels et al., "Sensitive and rapid assay on MT-4 cells for the detection of antiviral compounds against the AIDS virus", J. of Virological Methods 1987, 16: 171-185).

Luciferase activity was measured 96 hours later by adding a cell titer glo (Promega, Madison, Wis.). Percent inhibition of cell protection data was plotted relative to no compound control. Under the same condition, cytotoxicity of the compounds was determined using cell titer Glo™ (Promega, Madison, Wis.). $IC_{50}$s were determined from a 10 point dose response curve using 3-4-fold serial dilution for each compound, which spans a concentration range >1000 fold.

These values are plotted against the molar compound concentrations using the standard four parameter logistic equation:

$$y=((V\max*x\char`^n)/(K\char`^n+x\char`^n))+Y2$$

where:

Y2=minimum γ n=slope factor

Vmax=maximum γ x=compound concentration [M]

K=$EC_{50}$

When tested in the MT4 assay compounds were found to have $IC_{50}$ values listed in Table 1.

TABLE 1

| Example | $IC_{50}$ (uM) |
| --- | --- |
| 1 | 0.027 |
| 2 | 0.076 |
| 3 | 0.219 |
| 4 | 0.034 |
| 5 | 0.005 |
| 6 | 0.060 |
| 7 | 0.005 |
| 8 | 0.004 |
| 9 | 0.014 |
| 10 | 0.005 |
| 11 | 0.009 |
| 12 | 0.019 |
| 13 | 0.004 |
| 14 | 0.017 |
| 15 | 0.077 |
| 16 | 0.013 |
| 17 | 0.010 |
| 18 | 0.013 |
| 19 | 0.092 |
| 20 | 0.042 |
| 21 | 0.008 |
| 22 | 0.009 |

What is claimed is:

1. A compound of Formula I:

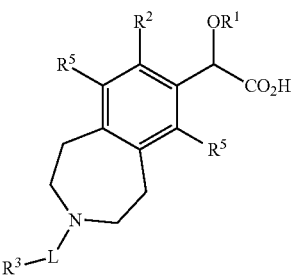

Formula I or a pharmaceutically acceptable salt thereof wherein:
$R^1$ is $C_{1-6}$alkyl;
$R^2$ is $C_{5-14}$aryl, $C_{3-7}$cycloalkyl, $C_{3-7}$cycloalkenyl, $C_{3-9}$heterocycle, or $C_{5-9}$heteroaryl, wherein each $R^2$ group is optionally substituted by one to four substituents selected from halo, $C_{1-6}$alkyl, $C_{1-6}$heteroalkyl, or $C_{1-6}$alkylene or $C_{1-6}$heteroalkylene wherein said $C_{1-6}$alkylene or $C_{1-6}$heteroalkylene are bonded to adjacent carbon atoms on said $C_{5-14}$aryl, $C_{3-7}$cycloalkyl, $C_{3-7}$cycloalkenyl, $C_{3-9}$heterocycle, or $C_{5-9}$heteroaryl to form a fused ring;
L is a bond —$C_{1-3}$alkylene-, —$SO_2$—, —C(O)—, —C(S)—, —C(NH)—, —C(O)NH—, —C(O)NHCH$_2$—, —C(O)OCH$_2$—, —C(O)O—, —C(O)C(O)—, —$SO_2$—NH—, or —CH$_2$C(O)—;
$R^3$ is H, CN, $C_{1-6}$alkyl, $C_{5-14}$aryl, CH$_2$$C_{5-14}$aryl, CH$_2$$C_{3-7}$cycloalkyl, $C_{3-7}$cycloalkyl, $C_{3-7}$spirocycloalkyl, $C_{3-7}$cycloalkenyl, $C_{3-9}$heterocycle, or $C_{5-9}$heteroaryl, wherein each $R^3$ group is optionally substituted by one to four substituents selected from halo, $C_{1-6}$alkyl, $C_{2-8}$bridgedheterocycle, $C_{3-7}$cycloalkyl, $C_{1-3}$fluoroalkyl, —OC$_{1-6}$alkyl, —C(O)$R^4$, —C(O)NR$^4$, —C(O)NHR$^4$, $C_{5-14}$aryl, $C_{1-6}$heteroalkyl, —B(OH)$_2$, $C_{3-9}$heterocycle, $C_{5-6}$heteroaryl, —C(O)OC$_{1-6}$alkyl, or two substituents bonded to adjacent atoms may bond together to form a fused ring and that fused ring may optionally be substituted with $R^4$, wherein $R^4$ is CN, halo, —OC$_{1-6}$alkyl, $C_{1-6}$alkyl, $C_{3-7}$cycloalkyl, $C_{3-9}$heterocycle, or $C_{5-14}$aryl;
each $R^5$ is independently H, halogen, $C_{1-6}$alkyl, or $C_{3-7}$cycloalkyl, wherein each $C_{1-6}$alkyl and $C_{3-7}$cycloalkyl may optionally be substituted with 1-3 halogen atoms; and
and wherein each heterocycle, heteroaryl, heteroalkyl, and heteroalkylene comprises one to three heteroatoms selected from S, N, B, or O.

2. A compound or salt according to claim 1 wherein $R^1$ is t-butyl.

3. A compound or salt according to claim 2 wherein $R^2$ is optionally substituted phenyl.

4. A compound or salt according to claim 3 wherein $R^1$ is phenyl substituted by one to four substituents selected from fluorine, methyl, —CH$_2$CH$_2$CH$_2$O— wherein said —CH$_2$CH$_2$CH$_2$O— is bonded to adjacent carbon atoms on said phenyl to form a bicyclic ring, or —NHCH$_2$CH$_2$O— wherein said —NHCH$_2$CH$_2$O— is bonded to adjacent carbon atoms on said phenyl to form a bicyclic ring.

5. A compound or salt according to claim 4 wherein L is —C(O)—.

6. A compound or salt according to claim 5 wherein $R^3$ is $C_{1-6}$alkyl, phenyl, naphthyl, cyclopentyl, cyclohexyl, pyridyl, or tetrahydropyranyl, each of which is optionally substituted by 1-3 substituents selected from halogen, $C_{1-6}$alkyl, —$OC_{1-6}$alkyl, $C_{1-3}$fluoroalkyl, or phenyl.

7. A compound or salt according to claim 6 wherein each $R^4$ is methyl.

8. A compound or salt according to claim 7 wherein the stereochemistry on the carbon to which $OR^1$ is bound is as depicted below

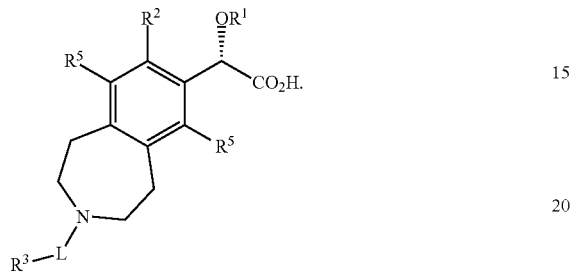

9. A pharmaceutical composition comprising a compound or salt according to claim 1.

10. A method for treating a viral infection in a patient mediated at least in part by a virus in the retrovirus family of viruses, comprising administering to said patient a composition according to claim 9.

11. The method of claim 10 wherein said viral infection is mediated by the HIV virus.

* * * * *